United States Patent [19]

Gregg

[11] Patent Number: 5,738,650
[45] Date of Patent: Apr. 14, 1998

[54] SUBARACHNOID NEEDLE AND METHOD FOR ADMINISTERING THERAPEUTIC AGENTS TO THE SUBARACHNOID SPACE

[75] Inventor: Joseph John Gregg, Hasbrouck Heights, N.J.

[73] Assignee: Becton, Dickinson and Company, Franklin Lakes, N.J.

[21] Appl. No.: 517,863

[22] Filed: Aug. 22, 1995

Related U.S. Application Data

[63] Continuation-in-part of Ser. No. 326,569, Oct. 20, 1994, Pat. No. 5,470,318, which is a continuation of Ser. No. 11,056, Jan. 29, 1993, abandoned.

[51] Int. Cl.$^6$ .................................................. A61M 31/00
[52] U.S. Cl. .......................... 604/51; 158/164; 158/272
[58] Field of Search ................................. 604/158, 162, 604/164, 167, 239, 272, 51, 49

[56] References Cited

U.S. PATENT DOCUMENTS

| | | |
|---|---|---|
| 2,862,495 | 12/1958 | Gewecke . |
| 4,411,657 | 10/1983 | Galindo . |
| 4,699,612 | 10/1987 | Hamacher . |
| 4,790,830 | 12/1988 | Hamacher . |
| 4,808,157 | 2/1989 | Coombs ............................ 604/158 |
| 4,838,877 | 6/1989 | Massau . |
| 5,024,655 | 6/1991 | Freeman et al. ............... 604/158 X |
| 5,085,631 | 2/1992 | Leighton ....................... 604/164 X |
| 5,098,389 | 3/1992 | Cappucci ........................ 604/158 |
| 5,100,390 | 3/1992 | Lubock et al. . |
| 5,160,323 | 11/1992 | Andrew ........................... 604/158 |
| 5,234,406 | 8/1993 | Drasner et al. . |
| 5,304,141 | 4/1994 | Johnston et al. ................ 604/158 |

FOREIGN PATENT DOCUMENTS

| | | |
|---|---|---|
| 0727187 | 8/1996 | European Pat. Off. . |
| 2262238 | 6/1993 | United Kingdom . |

*Primary Examiner*—Mark Bockelman
*Attorney, Agent, or Firm*—Arthur D. Dawson

[57] ABSTRACT

A method for introducing an injectable medicament into a subarachnoid space of a patient includes advancing a subarachnoid needle into the subarachnoid space. The subarachnoid needle has an elongate passage with a sidewall, a proximal end and a distal end that has a closed point and at least two openings through the sidewall located at a distance from the closed point. The method includes establishing a fluid communication between the subarachnoid space and the passageway through the openings, then introducing the medicament into the subarachnoid space of the patient through the passageway.

6 Claims, 7 Drawing Sheets

FIG-12

SUBARACHNOID NEEDLE AND METHOD FOR ADMINISTERING THERAPEUTIC AGENTS TO THE SUBARACHNOID SPACE

This application is a continuation in part of U.S. patent application Ser. No. 08/326,569 now U.S. Pat. No. 5,470,318, which is a continuation of U.S. patent application Ser. No. 08/011,056 filed Jan. 29, 1993, now abandoned.

BACKGROUND OF THE INVENTION

1. Field of Invention

The present invention relates to catheter/needle placement and more particularly to a subarachnoid needle and a method for its use in delivering medicaments into the subarachnoid space.

2. Description of Related Information

Generally speaking, there are two basic techniques for introducing injectable medicament into the spinal area of a patient. The techniques both can be used to create anesthesia: one being delivery of the medicament into the epidural space, "epidural," and the other, delivery into the subarachnoid space, "spinal" or "subarachnoid." The medicaments can be any type of injectable therapeutic material including antibiotics, steroids and the like, but generally are agents used for anesthesia and analgesia.

A survey of previous patent literature reports in this general area is found in U.S. Pat. No. 5,085,631 which teaches a method for placement of a subarachnoid catheter which utilizes a three component apparatus comprising an outer needle, an inner needle and a catheter intermediate the two needles.

A subarachnoid placement is recognized as providing a faster, more uniform distribution of an anesthetic agent, but several major side effects may result from improper subarachnoid placement.

Puncture of the dural membrane for entrance of a needle or catheter with a large gauge needle may result in postoperative leakage of cerebrospinal fluid from the puncture site, often resulting in severe headaches. When puncture of the dural membrane is made with a needle, a bolus introduction of the anesthetic agent generally is administered. The bolus results in rapid onset of anesthesia, but the anesthetic effect then generally lasts only a few hours. To overcome both the effects of a procedure requiring a large puncture of the dural membrane and the somewhat limited duration of subarachnoid bolus delivery, microcatheters were developed. The use of these microcatheters allowed intermittent instillation of the medicament for maintenance of the anesthetic effect and minimized the size of the dural puncture, thereby reducing the incidence of post procedure headaches. Microcatheters also present severe side effects. Since they are small and flexible, microcatheters have limited flow capacity, the limited flow capacity may hinder mixing the medicament with cerebrospinal fluid. Microcatheters are additionally prone to kinking and breakage. Further, there have been occurrences of permanent nerve damage with microcatheters, apparently as a result of high local concentrations of the medicament developing during delivery at adjacent branching nerves. This potential for nerve damage resulted in restrictions on the use of certain microcatheter procedures.

Subarachnoid placement of medicaments, if done properly, is acknowledged to be desirable. Thus, a method and device that would minimize the size of the puncture of the dural membrane, allow accurate and controlled placement of a therapeutically effective amount of a medicament within the subarachnoid space, thereby avoiding nerve damage, coupled with an ability to rapidly initiate and maintain a therapeutic level for longer procedures would represent an advance to the medical arts. A method and apparatus that addresses these needs constitute the present invention.

SUMMARY

A method of the present invention for introducing an injectable medicament into a subarachnoid space of a patient includes advancing a subarachnoid needle into the subarachnoid space. The subarachnoid needle has an elongate passage with a sidewall, a proximal end and a distal end that has a closed point and at least two openings through the sidewall located at a distance from the closed point. The method includes establishing a fluid communication between the subarachnoid space and the passageway through the at least two openings, then introducing the medicament into the subarachnoid space of the patient through the passageway and the at least two openings.

The method of the invention substantially avoids forming high localized concentrations of the medicament near nerves in the cauda equina by dispersing the medicament into the cerebro-spinal fluid through the at least two openings in the needle sidewall.

DETAILED DESCRIPTION

While this invention is satisfied by embodiments in many different forms, there is shown in the drawings and is herein described in detail preferred embodiments of the invention with the understanding that the present disclosure is to be considered exemplary of the principles of the invention and is not intended to limit the invention to the embodiments illustrated. The scope of the invention is measured by the appended claims and their equivalents.

For the purposes of the description of the present invention, the term "distal end" is meant to refer to the end of the assembly closest to the needle portion point, whereas the term "proximal end" is meant to refer to the end of the assembly furthest from the needle portion point.

Adverting to FIGS. 1–8, a catheter/needle assembly 10 of the present invention is used for introducing an injectable medicament into the subarachnoid space of a patient. The injectable medicament can be any type of liquid therapeutic agent, including antibiotics, steroids and the like, but generally are agents used for anesthesia and analgesia. The assembly 10 includes an elongate flexible tube portion 12 sized to fit within a bore 14 of an epidural needle 16. Tube 12 has a proximal end 18, a distal end 20 and a hollow bore 22. Assembly 10 also includes an elongate needle portion 24 having a distal point 26 and a passageway 28 therethrough in fluid communication with bore 22 of tube 12. Needle portion 24 is fit within bore 22, being fixedly attached to and fluidity sealing bore 22. Distal end 20 of flexible tube 12 forms a shoulder 30 that projects radially outwardly from needle portion 24.

Figure 1:
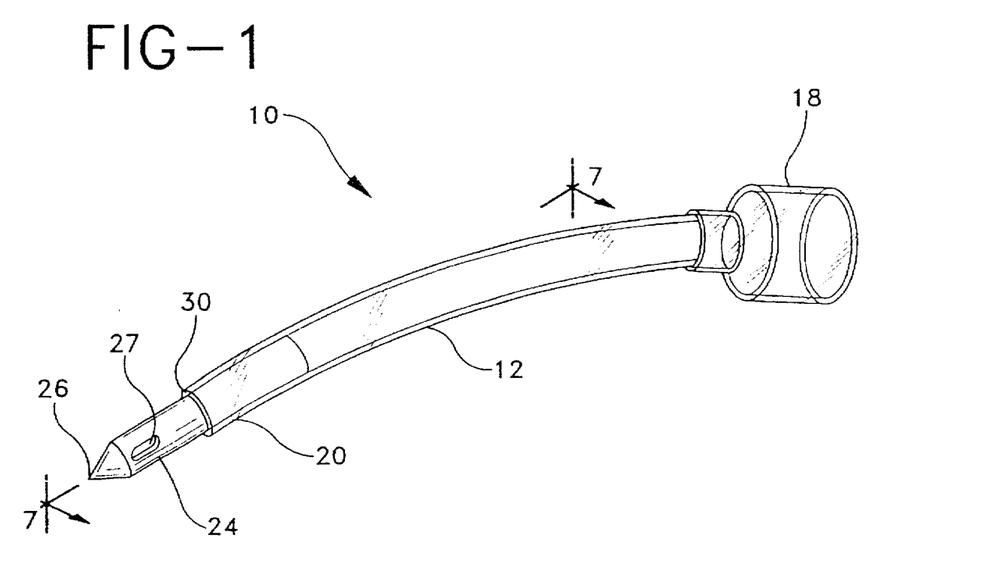
FIG. 1 is a perspective view of the catheter/needle assembly of the present invention.

Needle portion 24 is preferably formed from stainless steel, most preferably from stainless steel having the composition 304. Needle portion 24 has an overall length "A" that is preferably about 15 to 25 mm long and most preferably about 19 mm. Needle portion 24 projects from tube 12 a distance "B" that preferably is about 9 to 13 mm and most preferably is about 11 mm. Needle portion 24 is preferably 25 to 30 gauge and most preferably 27 gauge, about 11 mm. Needle portion 24 is preferably 25 to 30 gauge and most preferably 27 gauge. Needle portion 24 preferably has a pencil point configuration and at least one side opening 27. The side opening or openings combined with bore 22, which most preferably accommodates the 27 gauge needle and thus is larger than most bores of previously used microcatheters, are believed to facilitate mixing of the medicament with cerebrospinal fluid during the delivery and thereby substantially reduce nerve damage caused by high local medicament concentration.

One skilled in the art of needles will recognize that the sizing of hypodermic needles is commonly referred to a gauge table wherein the nominal sizing of the inner and outer diameters generally corresponds to:

Table of Hypodermic Tubing Nominal Sizes

| Gauge | Outside Diameter (mm) | Inside Diameter (mm) |
| --- | --- | --- |
| 30 | 0.30 | 0.18 |
| 29 | 0.33 | 0.20 |
| 28 | 0.36 | 0.20 |
| 27 | 0.40 | 0.25 |
| 26 | 0.46 | 0.30 |
| 25 | 0.51 | 0.30 |
| 24 | 0.56 | 0.36 |
| 23 | 0.64 | 0.38 |
| 22 | 0.71 | 0.46 |
| 21 | 0.82 | 0.56 |
| 20 | 0.90 | 0.65 |
| 19 | 1.08 | 0.80 |
| 18 | 1.27 | 0.96 |

-continued

Table of Hypodermic Tubing Nominal Sizes

| Gauge | Outside Diameter (mm) | Inside Diameter (mm) |
| --- | --- | --- |
| 17 | 1.50 | 1.17 |
| 16 | 1.65 | 1.32 |

Epidural needle 16 with bore 14, which tube 12 is sized to fit within, is sized from 16 to 25 gauge, with tube 12 being sized appropriately, for example, an epidural needle size 20 gauge with a tube portion size 0.6 mm and needle portion size 27 gauge. The overall length of assembly 10 from tube portion proximal end 18 to needle portion distal point 26 is preferably within 50 to 100 cm and most preferably has, for an adult patient, an overall length of about 76 cm. All dimensions of the most preferred embodiment present herein are intended for an average 70 kg adult. One skilled in the art of catheters, needles and hypodermic delivery devices will recognize that for specialty applications such as neonates, pediatric patients and other specialty applications, it may be desirable to reduce or increase sizes and length of some or all the components for the specific application.

Figure 2:
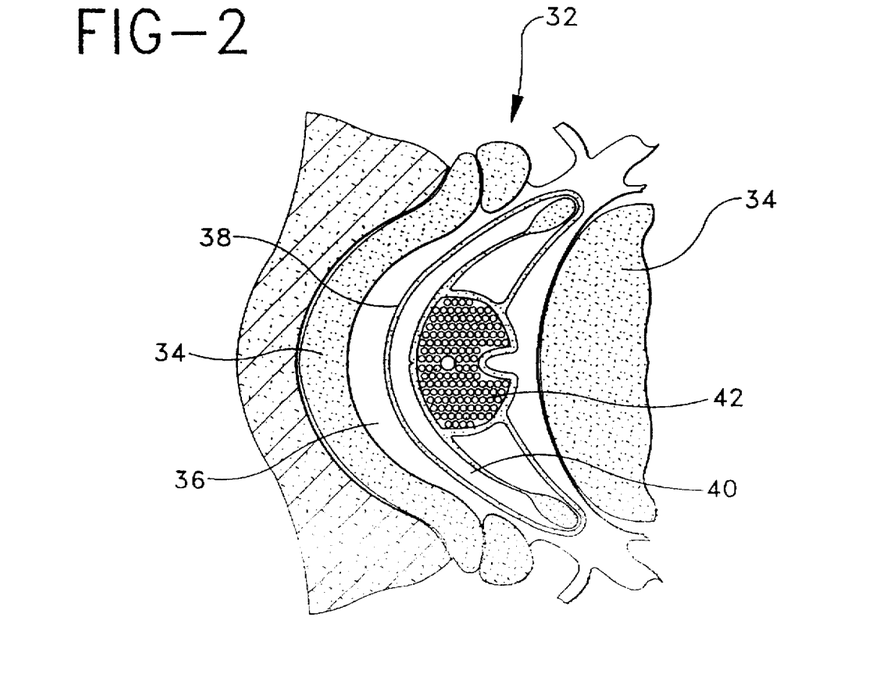
FIG. 2 is a horizontal cross-sectional view of a human spine.

A preferred method for use of assembly 10 can best be understood by reference to FIGS. 2–6. FIG. 2 shows a horizontal cross-section of a human spine 32, bone tissue 34, epidural space 36, dural membrane 38, subarachnoid space 40 and cauda equina 42. Adverting to FIGS. 3–6, a schematic vertical cross-section of spine 32 is shown with bone tissue sections 34 having ligamentous tissue 35 therebetween. Epidural needle 16 having a proximal hub, a bore 14 and a point 44 is introduced into epidural space 36 through ligamentous tissue 35 until point 44 is in close approximation to dural membrane 38. An opening 46 at distal point 44 to bore 14 of the epidural needle maybe occluded during insertion through the external skin and ligamentous tissue 35 by a suitable styler, (not shown) to avoid transporting fragments of tissue into epidural space 36. The stylet may then be removed and replaced with assembly 10.

Figure 5:
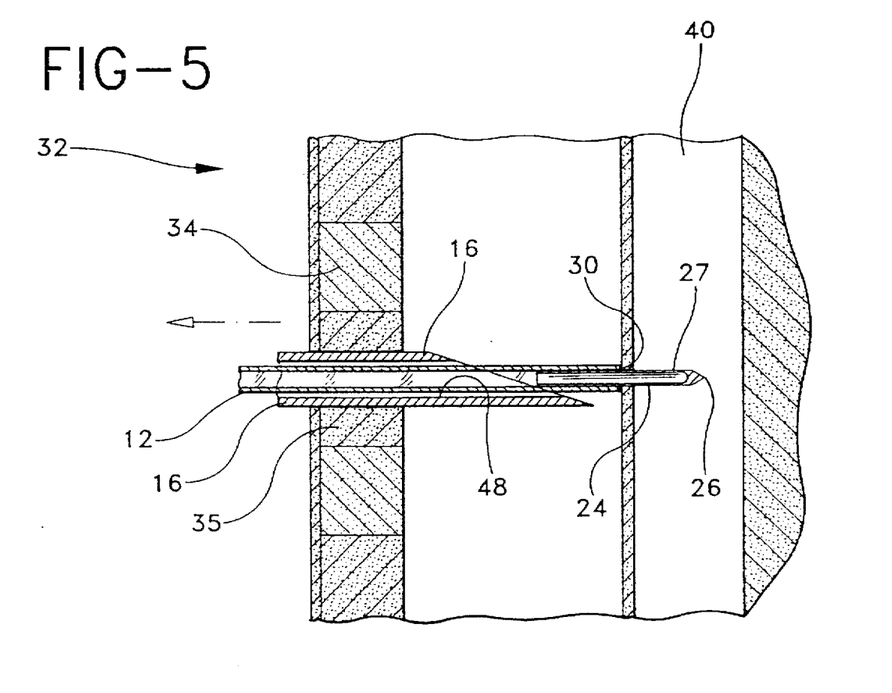
FIG. 5 is a schematic vertical cross-section of a human spine showing the advancement of the presently invented assembly through the bore of the epidural needle so that the needle portion penetrates the dural membrane.

Assembly 10 is then advanced within bore 14 of epidural needle 16 until needle portion 24 penetrates dural membrane 38 and tube bore 22 is in fluid communication with the subarachnoid space 40. The preferred embodiment of assembly 10 is generally placed in the lumbar region of the spine. In the lumbar region, subarachnoid space 40 contains the cauda equina 42, literally translated as "horse's tail". The reason for this name is that the spinal cord usually ends at the lower border of the first lumbar vertebra, becoming a series of discrete nerves contained within the dural sac. A preferred pencil point distal tip 26 of needle portion 24 will tend to separate rather than cut these discrete nerves.

Figure 6:
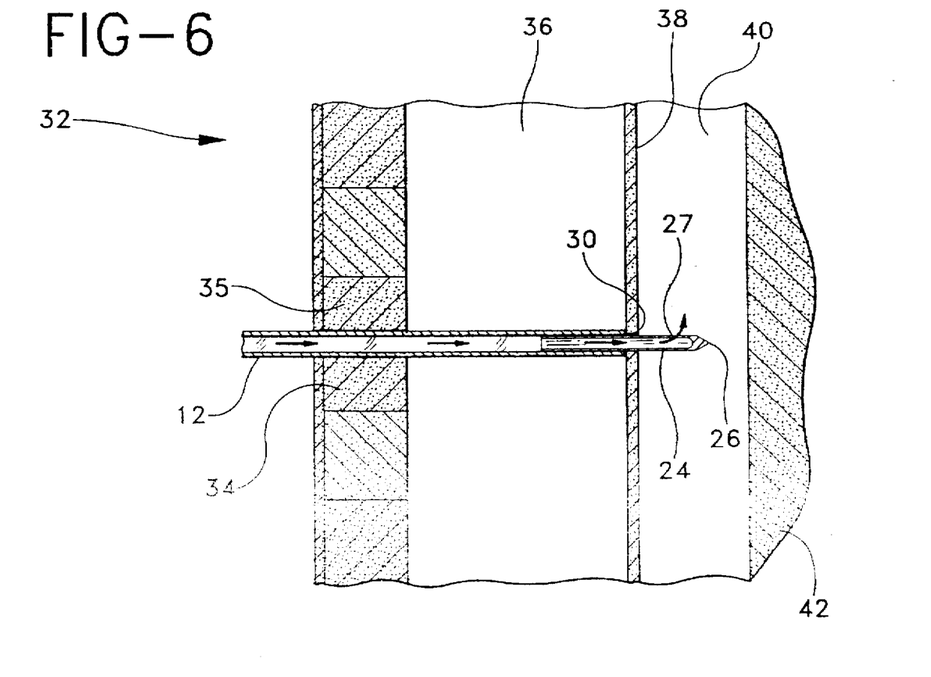
FIG. 6 is a schematic vertical cross-section of a human spine showing the presently invented assembly in position for delivery of a medicament into the subarachnoid space, the epidural needle having been removed.

Shoulder 30 at distal end 20 of tube 12 may indicate correct depth of penetration by substantially preventing further penetration of assembly 10 into dural membrane 38. Correct placement of needle portion 24 in subarachnoid space 40 may be further confirmed by withdrawal of cerebrospinal fluid through the assembly. Following the placement of assembly 10, epidural needle 16 may be removed leaving only assembly 10. An adapter, preferably a Tuohy-Borst type adapter and the like, and a medicament filter may be fitted to proximal end 18 of tube portion 12. A delivery device many then be attached and the desired medicament administered to the patient either as a bolus, intermittent dosing, continuous infusion or a combination of these administration techniques as appropriate for the procedure to be practiced.

A kit suitable for practicing the method described herein above may include epidural needle 16 and assembly 10.

Figure 7:
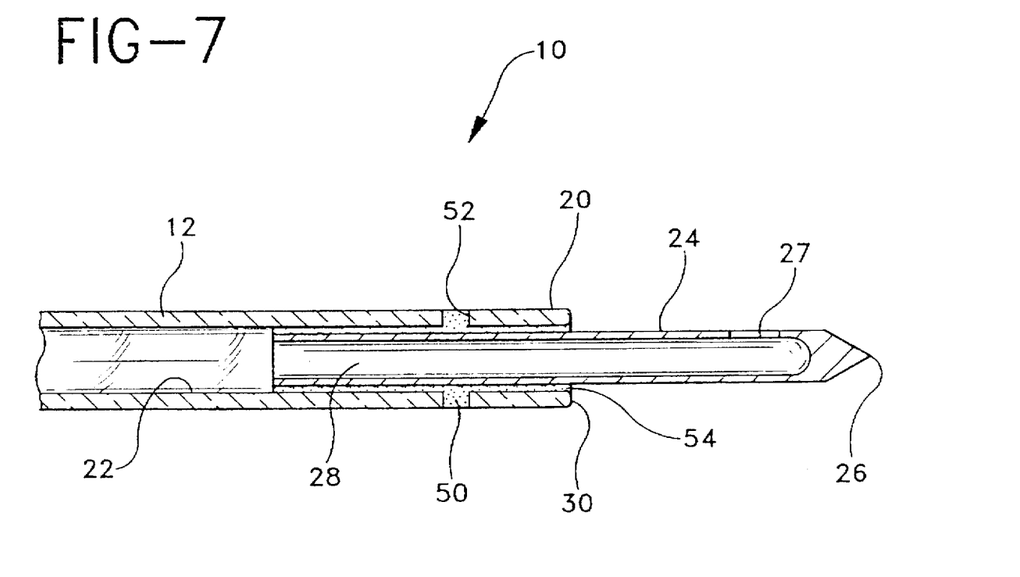
FIG. 7 is an enlarged cross-section of an embodiment of the distal portion of the assembly of the present invention.

Needle 16 is preferably an epidural needle with a straight bevel point formed at an angle of about 30 to 50 degrees to a longitudinal axis of the needle. More preferably, needle 16 is a Crawford type needle having a straight bevel point formed at an angle of about 40 degrees to the longitudinal axis of the needle and having a size about 20 gauge with a length of about 90 mm. Epidural needle 16 may include a removable stylet to occlude opening 46 at distal point 44. The function of a stylet in an epidural needle is to prevent coring of soft tissue by the large bore needle, which could result in transport of tissue particulates into the epidural space. Flexible tube portion 12 would then preferably be sized about 0.62 mm to fit within the 0.65 mm bore of the 20 g needle 16. Needle portion 24 would preferably be 27 gauge and fixedly attached within bore 22 of tube 12. Needle portion 24 preferably has pencil point type distal tip 26 and at least one side port opening to passageway 28. As is shown in FIG. 7. needle portion 24 may be adhesively bonded to tube bore 22 by adhesives such as cyanoacrylates, epoxies, hot-melts and the like. These adhesives must serve to form a bond between the tube material and the stainless steel needle portion, as well as sealing the tube bore to the needle bore.

Flexible tube 12 may be formed from a variety of flexible materials including polyamide, polyester, polyurethane, polytetrafluoroethylene and the like. The adhesive selection may be based the particular tubing material and assembly modes. As is shown in FIG. 7. formation of an adhesive bonding layer 50 between flexible tube 12 and needle portion 24 may be facilitated by at least one opening 52 located distally in tube portion 12 for introduction of the adhesive 50 into an overlap area 54 between the needle portion and the tube bore. Introduction of adhesive 50 through the sidewall substantially reduces incidence of needle portion passageway 28 being blocked by excess adhesive during assembly.

Figure 8:
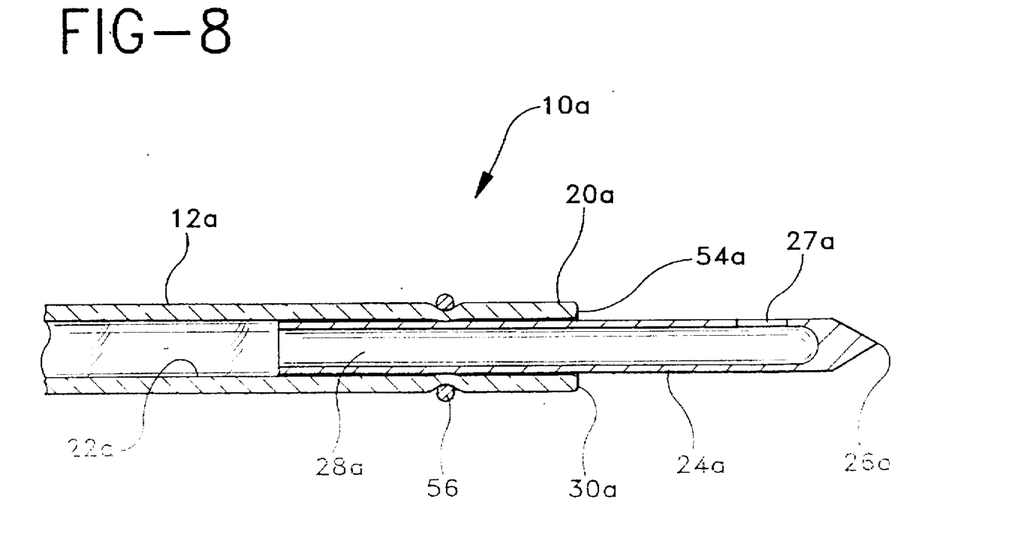
FIG. 8 is an enlarged cross-section of an alternate embodiment of the distal portion of the assembly of the present invention.

Referring now to FIG. 8, an alternative embodiment of the assembly is illustrated. In this alternative embodiment, the structure of the assembly is substantially similar to the embodiment shown in FIGS. 1–7. Accordingly, substantially similar components that perform substantially similar functions will be numbered identically to those components of the embodiment of FIGS. 1–7 except that a suffix "a" will be used to identify those components in FIG. 8.

Alternatively, needle portion 24a may be attached within bore 22a by means of at least one external band 56 crimped about tube 12a in the overlap area 54a with needle portion 24a. The crimped band serves to secure and seal portion 24a within tube bore 22a.

The kit may further include a guide wire stylet (not shown) to occlude needle port opening 27 and stiffen the assembly during the dural membrane penetration. The guide wire would then be removed to confirm placement by aspiration of cerebrospinal fluid. The kit may further include a filter for the medicament and an adapter to allow connection of a delivery device such as a syringe or infusion apparatus to the proximal end of the catheter. A Tuohy-Borst type adapter would be preferred. Additionally, the kit may include disinfectant skin preparation pads, adhesive tape, gloves and the like, if desired. The kit may be sealed in a package which provides a shelf package resistant to microorganisms, exposed to conditions such as ionizing radiation, sterilant gas and the like; the exposure would render any microorganisms contained within the package non-viable. Rendering any microorganisms present nonviable would thus provide a sterile ready-to-use procedure kit. One skilled in the art will recognize the necessity of ensuring that the materials used in the kit and the adhesive would be tolerant of the sterilization conditions and compatible with each other.

Referring to FIGS. 9–12, another embodiment of the present invention is shown. In this embodiment, some elements of the structure are substantially similar to those illustrated in FIGS. 1–8. Accordingly, substantially similar components that perform substantially similar functions are numbered similarly to those of FIGS. 1–8 except that a "hundreds" prefix is used to identify those components in FIGS. 9–12. For continuity, all other components in FIGS. 9–12 also use "hundreds" prefixes.

Figure 9:
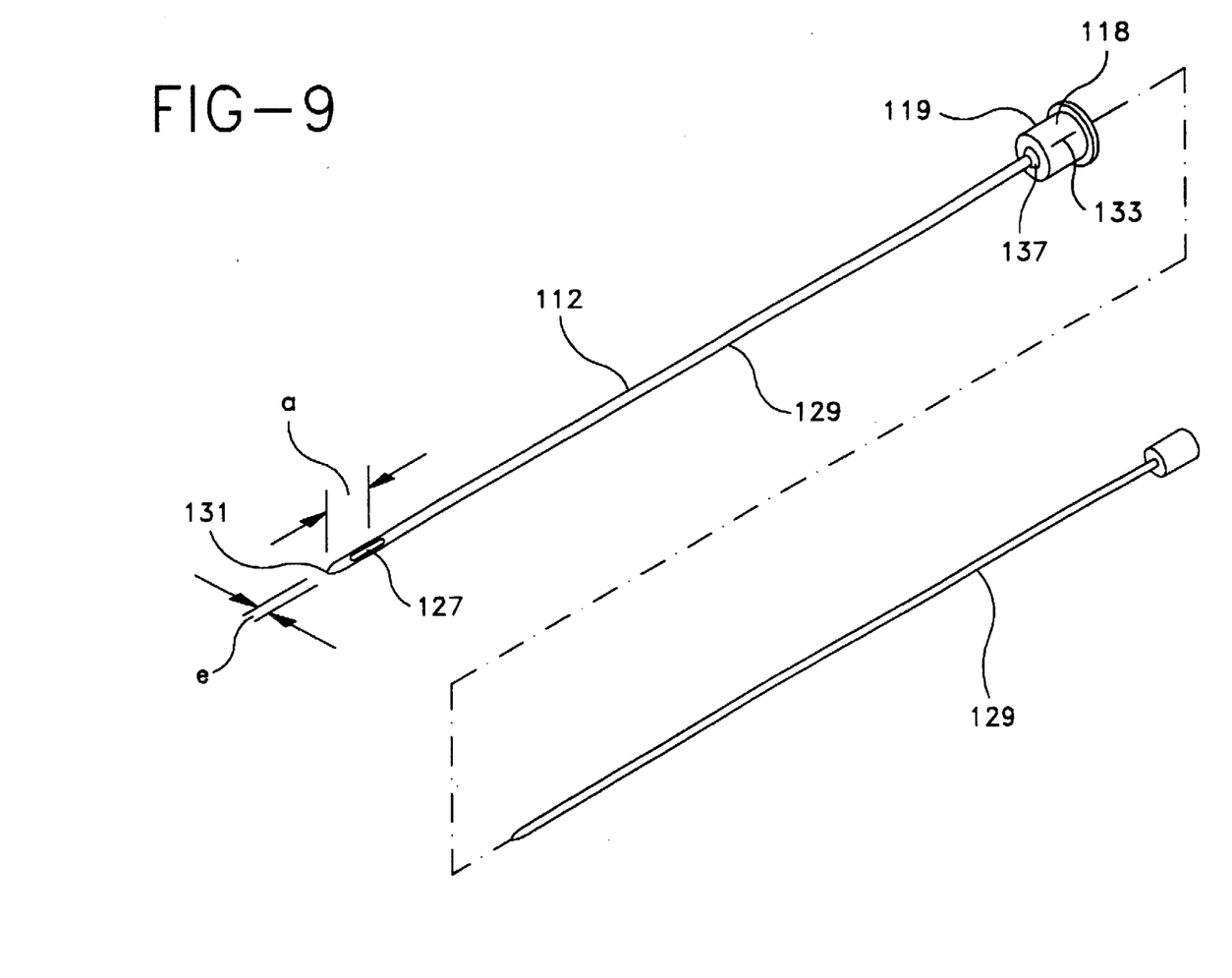
FIG. 9 is a perspective view of a subarachnoid needle of the present invention and a stylet.

FIG. 9 shows a subarachnoid needle 124 of the present invention that is useful for introducing an injectable medicament into the subarachnoid space of a patient. Subarachnoid needle 124 includes an elongate passageway 128 with a sidewall 129 and a proximal end 118 with a hub 119. Needle 124 has a distal end 126 with a closed point 131 and at least two openings 127 through sidewall 129 located a distance "a" from closed point 131. Preferably, distance "a," which is the distance from a center of opening 127 to closed point 131, is between about 2 mm to about 3 mm. There are at least two openings 127 through sidewall 129. When there are two openings 127, preferably the openings are arranged diametrically across from each other. Hub 119 preferably includes an indicia 133 in the form of a slot 137 aligned with openings 127 so that a practitioner may determine an alignment direction of the openings when needle 124 is placed in the subarachnoid space of the patient. Subarachnoid needle 124 also may include an obturator or stylet 129 fit within elongate passageway 128 to occlude openings 127.

Figure 10:
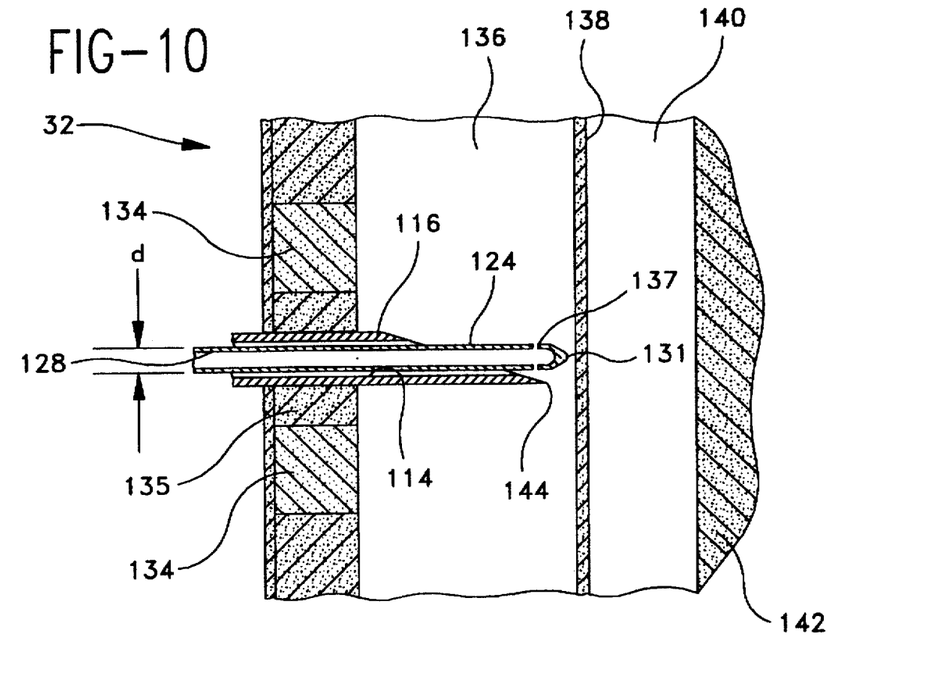
FIG. 10 a schematic vertical cross-section of a human spine showing the introduction of the subarachnoid needle of FIG. 9 into the bore of the epidural needle of FIG. 3.
Figure 11:
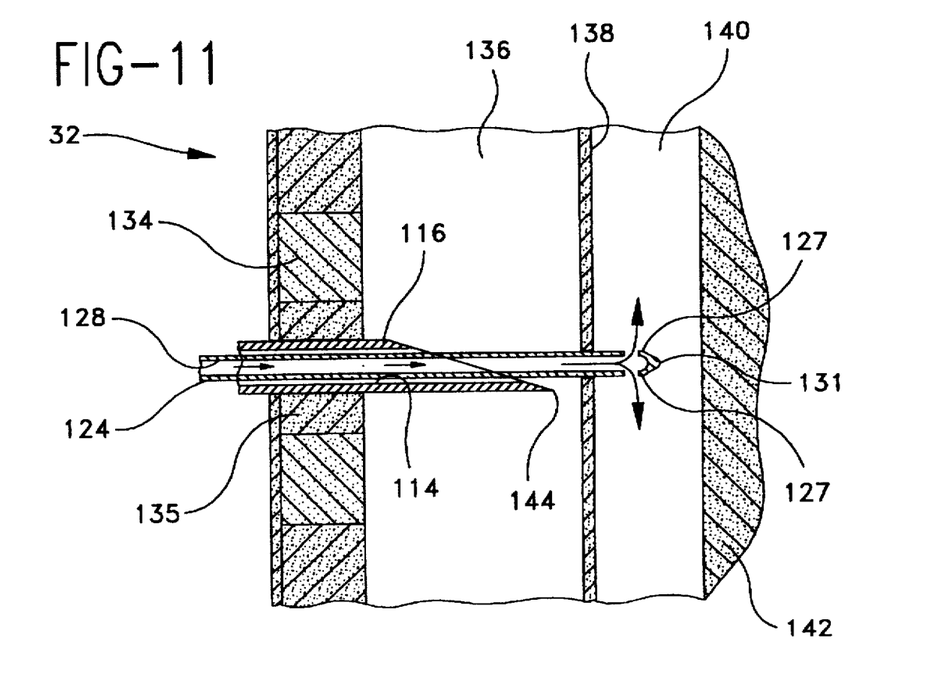
FIG. 11 is a schematic vertical cross-section of a human spine showing the advancement of the subarachnoid needle of FIG. 9 through the bore of the epidural needle so that the distal end penetrates the dural membrane.

Subarachnoid needle 124 may also be used with an epidural needle 116 or similar needle, used as an introducer as shown in FIGS. 10 and 11. As described above and illustrated in FIG. 3 for the needle portion 24 of assembly 10, in this embodiment subarachnoid needle 124 has an external diameter "e" less than an inside diameter "d" of epidural needle 116. Subarachnoid needle 124 is sized from 22 gauge to about 30 gauge (see table above). Preferably needle 124 is 27 gauge and formed from stainless steel. When the preferred 27 gauge subarachnoid needle 124 with two openings 127 is placed in the subarachnoid space and the medicament is administered, the medicament is substantially dispersed through both openings 127, as indicated in FIG. 11 by flow arrows, into the cerebro-spinal fluid substantially reducing nerve damage caused by high local concentrations of medicament as described above.

Figure 3:
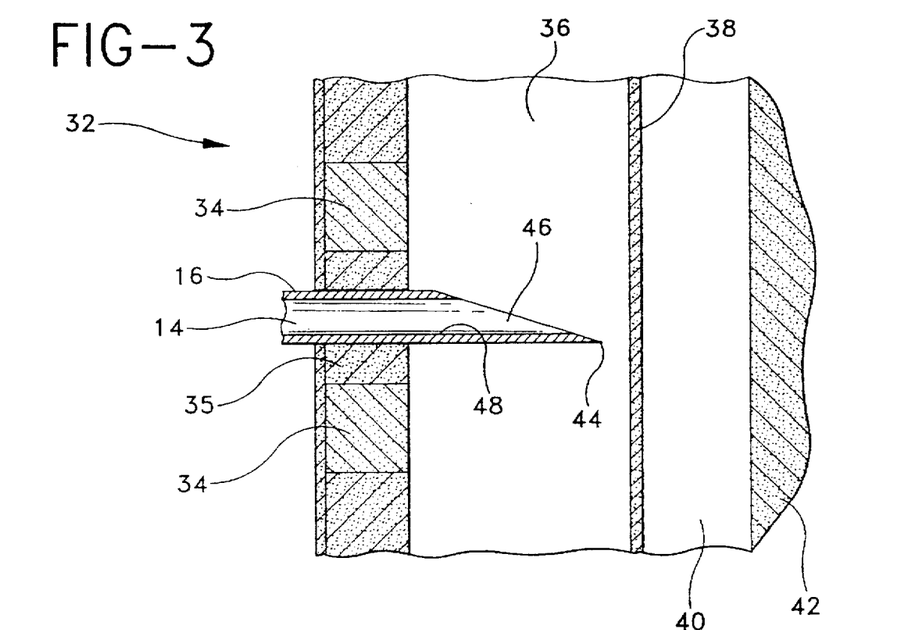
FIG. 3 is a schematic vertical cross-section of a human spine showing the placement of an epidural needle.
Figure 4:
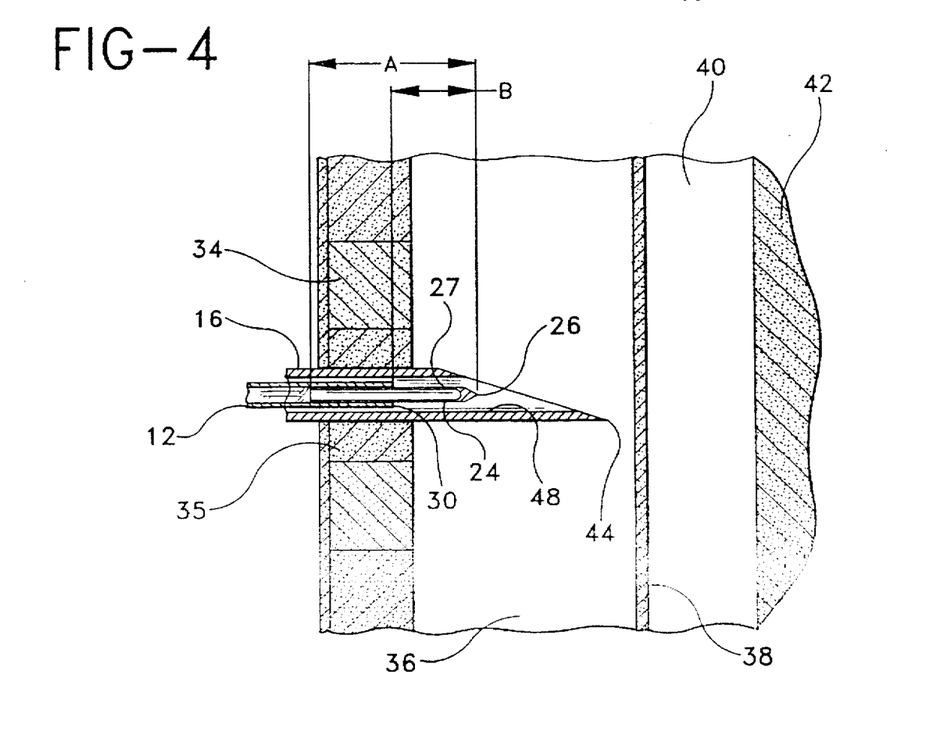
FIG. 4 is a schematic vertical cross-section of a human spine showing the introduction of the presently invented catheter/needle assembly into the bore of the epidural needle.

Referring to FIG. 3, a preferred method of the present invention for introducing an injectable medicament into the subarachnoid space of a patient includes placing an elongate introducer 16 having distal point 44 and hollow bore 14 into epidural space 35 of the patient. The method includes positioning the introducer so that distal point 44 is in close approximation to dural membrane 38 of the patient as shown in FIG. 3.

Similarly, as illustrated in FIGS. 10 and 11, the method of the present invention includes placing an elongate introducer 116 having distal point 144 and hollow bore 114 with an inside diameter "d" into epidural space 135 of the patient and positioning the introducer so that distal point 144 is in close approximation to dural membrane 138 of the patient as shown in FIG. 10. The method then includes positioning subarachnoid needle 124 with an external diameter "e" less than inside diameter "d" of introducer 116 into hollow bore 114 of the introducer, advancing subarachnoid needle 124 through hollow bore 114 of the introducer until distal end 126 of the subarachnoid needle penetrates dural membrane 138 of the patient into the subarachnoid space of the patient. Preferably needle 124 is advanced until closed point 126 is more than about 3.3 mm into the subarachnoid space so that openings 127 are inside the dural membrane 138. The preferred method includes establishing a fluid communication between subarachnoid space 140 and passageway 128 through openings 127. Preferably, cerebro-spinal fluid is withdrawn from subarachnoid space 140 confirming that passageway 128 is in fluid communication with the subarachnoid space. Preferably the practitioner of the method then observes indicia 133 on hub 119 of the subarachnoid needle, rotating the needle and orienting openings 127 substantially parallel to a longitudinal axis of the patient's spinal cord. The method then includes introducing the medicament into the subarachnoid space of the patient as illustrated by the flow arrows in FIG. 11. By following the preferred method and aligning openings 127 substantially parallel to the patient's spinal cord, the practitioner substantially ensures that when the medicament is introduced into the subarachnoid space, the medicament is well dispersed into the cerebro-spinal fluid substantially reducing incidence of nerve damage due to high local concentrations of medicament.

The method of the present invention may also include a step of placing stylet 129 in passageway 128 and occluding openings 127 prior to the step of advancing the subarachnoid needle into the subarachnoid space. In the situation where stylet 129 is used, the step of introducing the medicament is preceeded by a step including removing the stylet from the passageway.

Figure 12:
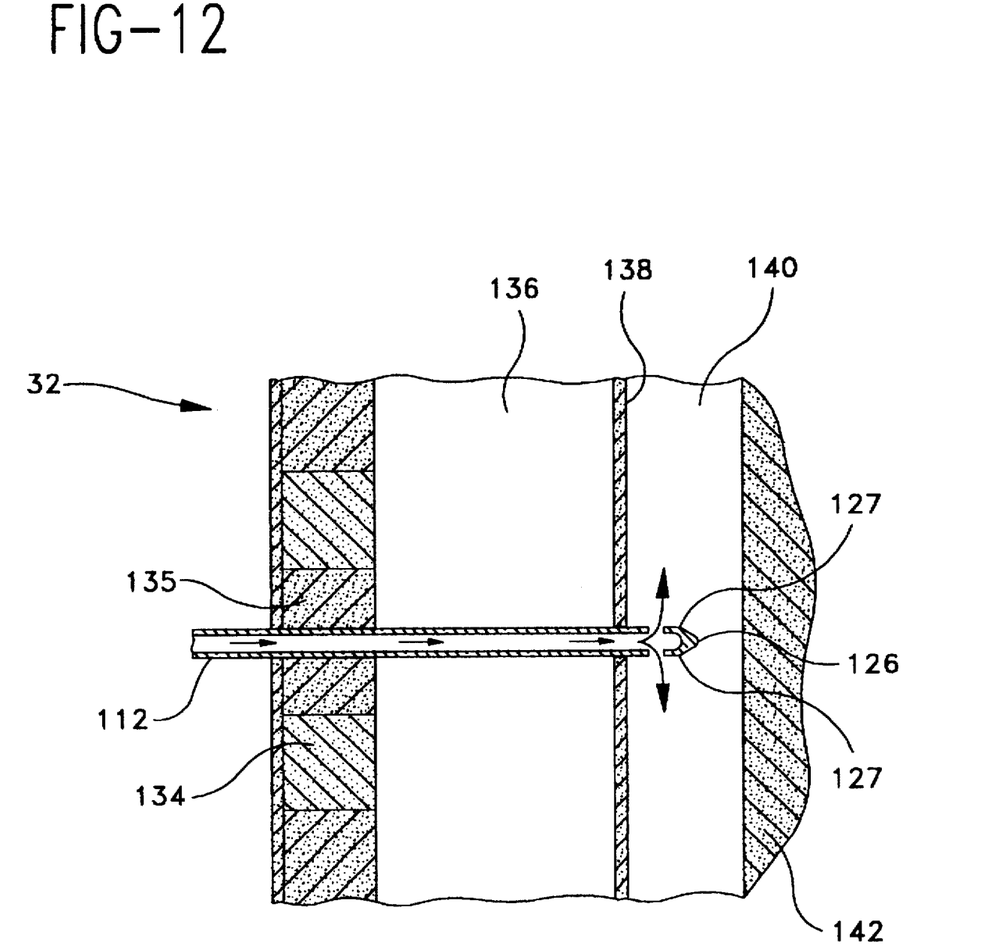
FIG. 12 is a schematic vertical cross-section of a human spine showing direct placement of the subarachnoid needle of FIG. 9 with the distal end penetrating the dural membrane.

For particular applications and to satisfy individual practitioner preferences, particular steps of the preferred method may be omitted or practiced in a different order. These alternatives are considered to be within the scope of the present invention. A non-limitive example of one of these alternative methods for introduction of a medicament into the subarachnoid space includes, as is illustrated in FIG. 12, placing subarachnoid needle 124 directly into subarachnoid space 140 without use of introducer 116, establishing fluid communication with the subarachnoid space through openings 127 and introducing the medicament into the subarachnoid space through passageway 128.

Thus it can be seen that the presently invented subarachnoid needle with at least two openings at the distal end provides an improvement to the art of delivery of medicaments to the subarachnoid space and addresses the problems present in the earlier used devices and techniques.

What is claimed is:

1. A method for introducing an injectable medicament into a subarachnoid space of a patient comprising:

placing an elongate introducer having a distal point and a hollow bore therethrough into an epidural space of the patient until said distal point is in close approximation to a dural membrane of the patient, said bore of said introducer having an internal diameter larger than an external diameter of a subarachnoid needle;

providing a subarachnoid needle having an external diameter and comprising an elongate passageway having a sidewall, a proximal end and a distal end including a closed point, said subarachnoid needle having two diametrically opposed openings through said sidewall located a distance from said closed point;

positioning said distal end of said subarachnoid needle into said bore of said introducer;

advancing said subarachnoid needle through said bore of said introducer until said distal end of said subarachnoid needle penetrates the dural membrane of the patient;

establishing a fluid communication between the subarachnoid space and said passageway through said openings; and introducing a medicament into the subarachnoid space of the patient through said passageway through said two openings.

2. The method of claim 1 wherein said introducing step is preceded by a step of withdrawing cerebra-spinal fluid from the subarachnoid space through said passageway of said subarachnoid needle thereby confirming that said passageway is in fluid communication with the subarachnoid space of the patient.

3. The method of claim 1 wherein said advancing step further comprises advancing said subarachnoid needle into said subarachnoid space more than about 3.3 mm, said distance from a center of each of said openings to said closed point being between about 2 mm to about 3 mm so that said passageway is in fluid communication with the subarachnoid space when said advancing of said subarachnoid needle into the subarachnoid space is more than about 3.3 mm.

4. The method of claim 1 wherein said subarachnoid needle further includes a hub attached to said proximal end of said needle, said hub having an indicia for providing an indication of an alignment direction of said openings; and said introducing step of said medicament is preceded by an orienting step comprising:

observing said indicia on said hub; and rotating said subarachnoid needle so that said indicia indicates an orientation of said openings substantially parallel to an axis of the patient's spinal cord.

5. A method for introducing an injectable medicament into a subarachnoid space of a patient comprising providing a subarachnoid needle having an external diameter and comprising an elongate passageway having a sidewall, a proximal end and a distal end including a closed point, said subarachnoid needle having two diametrically opposed openings through said sidewall located a distance from said closed point;

placing a stylet in said passageway of said subarachnoid needle;

advancing said subarachnoid needle into a subarachnoid space of a patient.;

removing said stylet;

establishing a fluid communication between the subarachnoid space and said passageway through said openings; and introducing a medicament into the subarachnoid space of the patient through said passageway and said two openings.

6. A method for introducing a medicament into a subarachnoid space of a patient comprising:

placing an elongate introducer having a distal point and a hollow bore therethrough into an epidural space of a patient so that said distal point is in close approximation to a dural membrane of the patient, said bore of said introducer having an inside diameter;

positioning a subarachnoid needle having an external diameter less than said inside diameter of said bore of said introducer into said bore of said introducer, said subarachnoid needle having an elongate passageway with a sidewall, a proximal end and a distal end comprising a closed point with two openings through said sidewall located a distance from said closed point, and said subarachnoid needle further including a hub having an indicia for providing an indication of an alignment direction of said openings attached to said proximal end of said needle;

advancing said subarachnoid needle through said bore of said introducer until said distal end of said subarachnoid needle penetrates the dural membrane of the patient.

establishing a fluid communication between the subarachnoid space and said passageway through said openings;

withdrawing cerebro-spinal fluid from the subarachnoid space through said passageway of said subarachnoid needle thereby confirming that said passageway is in fluid communication with the subarachnoid space of the patient;

observing said indicia on said hub;

rotating said subarachnoid needle so that said indicia indicates an orientation of said openings substantially parallel to an axis of the patient's spinal cord; and introducing a medicament into the subarachnoid space of the patient through said passageway.

\* \* \* \* \*